US00PP29840P3

(12) United States Plant Patent
Barends

(10) Patent No.: US PP29,840 P3
(45) Date of Patent: Nov. 13, 2018

(54) ***OSTEOSPERMUM* PLANT NAMED 'DUEOSTMAORFLAR'**

(50) Latin Name: *Osteospermum ecklonis*
Varietal Denomination: Dueostmaorflar

(71) Applicant: DUMMEN GROUP B.V., De Lier (NL)

(72) Inventor: Eveline Barends, De Lier (NL)

(73) Assignee: Dümmen Group B.V., De Lier (NL)

( * ) Notice: Subject to any disclaimer, the term of this patent is extended or adjusted under 35 U.S.C. 154(b) by 44 days.

(21) Appl. No.: 15/530,654

(22) Filed: Feb. 16, 2017

(65) Prior Publication Data

US 2018/0235131 P1 Aug. 16, 2018

(51) Int. Cl.
*A01H 5/02* (2018.01)

(52) U.S. Cl.
USPC ..... Plt./360

(58) Field of Classification Search
USPC ..... Plt./263.1, 360
See application file for complete search history.

*Primary Examiner* — Susan Beth McCormick Ewoldt
*Assistant Examiner* — Karen M Redden
(74) *Attorney, Agent, or Firm* — C. A. Whealy

(57) ABSTRACT

A new and distinct cultivar of *Osteospermum* plant named 'Dueostmaorflar', characterized by its uniform and mounding plant habit; medium in size; moderately vigorous growth habit; freely and uniformly branching habit; freely and early flowering habit; large single-type inflorescences with greyed orange and yellow orange bi-colored ray florets; and good garden performance.

1 Drawing Sheet

Botanical designation: *Osteospermum ecklonis.*
Cultivar denomination: 'DUEOSTMAORFLAR'.

BACKGROUND OF THE INVENTION

The present invention relates to a new and distinct cultivar of *Osteospermum* plant, botanically known as *Osteospermum ecklonis*, and hereinafter referred to by the name 'Dueostmaorflar'.

The new *Osteospermum* plant is a product of a planned breeding program conducted by the Inventor in Rheinberg, Germany and De Lier, The Netherlands. The objective of the program is to create and develop new vigorous *Osteospermum* plants that are freely and uniformly branching with numerous large inflorescences with unique and attractive ray and disc floret coloration.

The new *Osteospermum* plant originated from a cross-pollination by the Inventor of two unidentified proprietary selections of *Osteospermum ecklonis*, not patented. The new *Osteospermum* plant was discovered and selected by the Inventor as a single flowering plant within the progeny of the stated cross-pollination in a controlled greenhouse environment in De Lier, The Netherlands in July, 2013.

Asexual reproduction of the new *Osteospermum* plant by terminal vegetative cuttings in a controlled greenhouse environment in De Lier, The Netherlands since August, 2013 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dueostmaorflar'. These characteristics in combination distinguish 'Dueostmaorflar' as a new and distinct *Osteospermum* plant:

1. Uniform and mounding plant habit.
2. Medium in size, moderately vigorous growth habit.
3. Freely and uniformly branching habit.
4. Freely and early flowering habit.
5. Large single-type inflorescences with greyed orange and yellow orange bi-colored ray florets.
6. Good garden performance.

Plants of the new *Osteospermum* differ primarily from plants of the female parent selection in plant and growth habit as plants of the new *Osteospermum* are denser, stronger and more vigorous than plants of the female parent selection.

Plants of the new *Osteospermum* differ primarily from plants of the male parent selection in ray floret color as plants of the male parent selection have yellow-colored ray florets.

Plants of the new *Osteospermum* can be compared to plants of the *Osteospermum ecklonis* 'Fidostsu15', not patented. In side-by-side comparisons, plants of the new *Osteospermum* differ primarily from plants of 'Fidostsu15' in the following characteristics:

1. Plants of the new *Osteospermum* are more vigorous than plants of 'Fidostsu15'.
2. Plants of the new *Osteospermum* have longer and thicker lateral branches with shorter internodes than plants of 'Fidostsu15'.
3. Plants of the new *Osteospermum* have larger inflorescences than plants of 'Fidostsu15'.

4. Plants of the new *Osteospermum* and 'Fidostsu15' differ in ray floret color as ray florets of plants of 'Fidostsu15' are more bronze in color.
5. Plants of the new *Osteospermum* have longer peduncles than plants of 'Fidostsu15'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant.

The photograph is a side perspective view of a typical flowering plant of 'Dueostmaorflar' grown in a container.

DETAILED BOTANICAL DESCRIPTION

The aforementioned photograph, following observations and measurements describe plants grown during the summer in 25-cm containers in a glass-covered greenhouse in Rheinberg, Germany and under cultural practices typical of commercial *Osteospermum* production. During the production of the plants, day temperatures ranged from 17° C. to 30° C., night temperatures ranged from 10° C. to 20° C. and light levels averaged 135 watt/m$^2$. Plants were eight weeks old when the photograph was taken and 25 weeks old when the description was taken. In the following description, color references are made to The Royal Horticultural Society Colour Chart, 1995 and 2007 Editions, except where general terms of ordinary dictionary significance are used.

Botanical classification: *Osteospermum ecklonis* 'Dueostmaorflar'.

Parentage:

*Female, or seed, parent*.—Unidentified proprietary selection of *Osteospermum ecklonis*, not patented.

*Male, or pollen, parent*.—Unidentified proprietary selection of *Osteospermum ecklonis*, not patented.

Propagation:

*Type*.—Terminal vegetative cuttings.

*Time to initiate roots, summer*.—About 18 days at temperatures about 22° C. to 30° C.

*Time to initiate roots, winter*.—About 21 days at temperatures about 22° C. to 30° C.

*Time to produce a rooted cutting, summer*.—About 25 days at temperatures about 22° C. to 30° C.

*Time to produce a rooted cutting, winter*.—About 28 days at temperatures about 20° C. to 25° C.

*Root description*.—Medium in thickness, fibrous; typically grey white in color, actual color of the roots is dependent on substrate composition, water quality, fertilizers, substrate temperature and age of roots.

*Rooting habit*.—Moderately freely branching; medium density.

Plant description:

*Plant form and growth habit*.—Uniform and mounding plant habit; relatively short internodes, dense and bushy growth habit; medium in size; moderately vigorous growth habit.

*Plant height*.—About 39 cm.

*Plant diameter*.—About 82 cm.

*Lateral branches*.—Quantity per plant: Freely branching habit, about eight lateral branches developing per plant; pinching enhances lateral branch development. Length: About 32 cm. Diameter: About 9 mm. Internode length: About 7 mm. Strength: Strong, sturdy. Texture: Smooth, glabrous. Color: Close to 144C.

*Leaf description*.—Arrangement: Alternate, simple. Length: About 6.8 cm. Width: About 3.3 cm. Shape: Spatulate. Apex: Acute. Base: Attenuate. Margin: Dentate; sinuses divergent. Texture, upper and lower surfaces: Smooth, glabrous; leathery. Venation pattern: Pinnate. Color: Developing leaves, upper surface: Close to 137B. Developing leaves, lower surface: Close to 144A. Fully expanded leaves, upper surface: Close to 137A; venation, close to 144B. Fully expanded leaves, lower surface: Close to 137B to 137C; venation, close to 144B. Petioles: Length: About 8 mm. Diameter: About 0.6 mm. Texture, upper and lower surfaces: Smooth, glabrous. Color, upper surface: Close to 144A to 144B. Color, lower surface: Close to 144B.

Inflorescence description:

*Appearance and aspect*.—Terminal and axillary inflorescences; inflorescences positioned beyond the foliar plane on strong peduncles and face mostly upright to outwardly; single-type inflorescence form with lanceolate-shaped ray florets and tubular disc florets; ray and disc florets developing acropetally on a capitulum.

*Flowering habit*.—Freely flowering habit; about 130 inflorescences developing per plant.

*Fragrance*.—None detected.

*Flowering response*.—In Germany, plants of the new *Osteospermum* flower continuously from spring until first frost in the autumn; early flowering habit, plants begin flowering about six weeks after planting.

*Inflorescence longevity*.—Inflorescences last about three weeks on the plant; inflorescences not persistent.

*Inflorescence buds, just prior to anthesis*.—Height: About 2.1 cm. Diameter: About 1.4 cm. Shape: Ovoid. Color: Close to 137B and 144C.

*Inflorescence size*.—Diameter: About 7.1 cm. Depth (height): About 2 cm to 4 cm. Disc diameter: About 1.6 cm. Receptacle diameter: About 9 mm. Receptacle height: About 8 mm.

*Ray florets*.—Length: About 2.9 cm. Width: About 1 cm. Shape: Lanceolate. Apex: Emarginate. Base: Obtuse. Margin: Entire. Aspect: Mostly flat. Texture, upper and lower surfaces: Smooth, glabrous. Quantity per inflorescence and arrangement: About 27 arranged in two whorls. Color: When opening, upper surface: Towards the apex, close to N163A; towards the base, close to 14A with thin stripes, close to N163C. When opening, lower surface: Close to 165A. Fully opened, upper surface: Towards the apex, close to N163B; towards the base, close to 14A with thin stripes, close to N163C; with development color towards the base becoming closer to 12A with thin stripes, close to N163C. Fully opened, lower surface: Close to 165A; color does not change with development.

*Disc florets*.—Shape: Tubular with five pointed apices. Length: About 5 mm. Diameter, at the apex: About 2 mm. Diameter, at the base: About 1 mm. Number of disc florets per inflorescence: About 50. Color, immature and mature: Towards the apex, close to 178A; mid-section, close to 1D; towards the base, close to NN155B; mid-section becoming closer to NN155B with development.

*Phyllaries*.—Quantity per inflorescence and arrangement: About 19 arranged in one to two whorls. Length: About 9 mm. Width: About 1.4 mm. Shape: Lanceolate. Apex: Apiculate. Base: Attenuate. Margin: Entire. Texture, upper and lower surfaces: Smooth, glabrous; leathery. Color, upper surface: Close to 137B to 137C. Color, lower surface: Close to 137C.

*Peduncles*.—Length: About 13 cm. Diameter: About 2 mm. Strength: Strong. Aspect: Mostly upright to outwardly slanting. Texture: Smooth, glabrous. Color: Close to 143A.

*Reproductive organs*.—Androecium: Present on disc florets only. Anther shape: Oval. Anther length: About 2 mm. Anther color: Close to 79A to 79B. Pollen amount: Abundant. Pollen color: Close to 23A. Gynoecium: Present on both ray and disc florets. Pistil length: About 7 mm. Stigma shape: Bi-parted. Stigma color: Close to 79A. Style length: About 3 mm. Style color: Close to 79A. Ovary color: Close to 144C.

*Seeds*.—Length: About 7 mm. Diameter: About 3 mm. Texture: Smooth, glabrous. Color: Close to 199A.

Disease & pest resistance: Plants of the new *Osteospermum* have not been observed to be resistant to pathogens and pests common to *Osteospermum* plants.

Garden performance: Plants of the new *Osteospermum* have been observed to have good garden performance and to tolerate rain, wind and temperatures ranging from about 5° C. to about 35° C.

It is claimed:

1. A new and distinct *Osteospermum* plant named 'Dueostmaorflar' as illustrated and described.

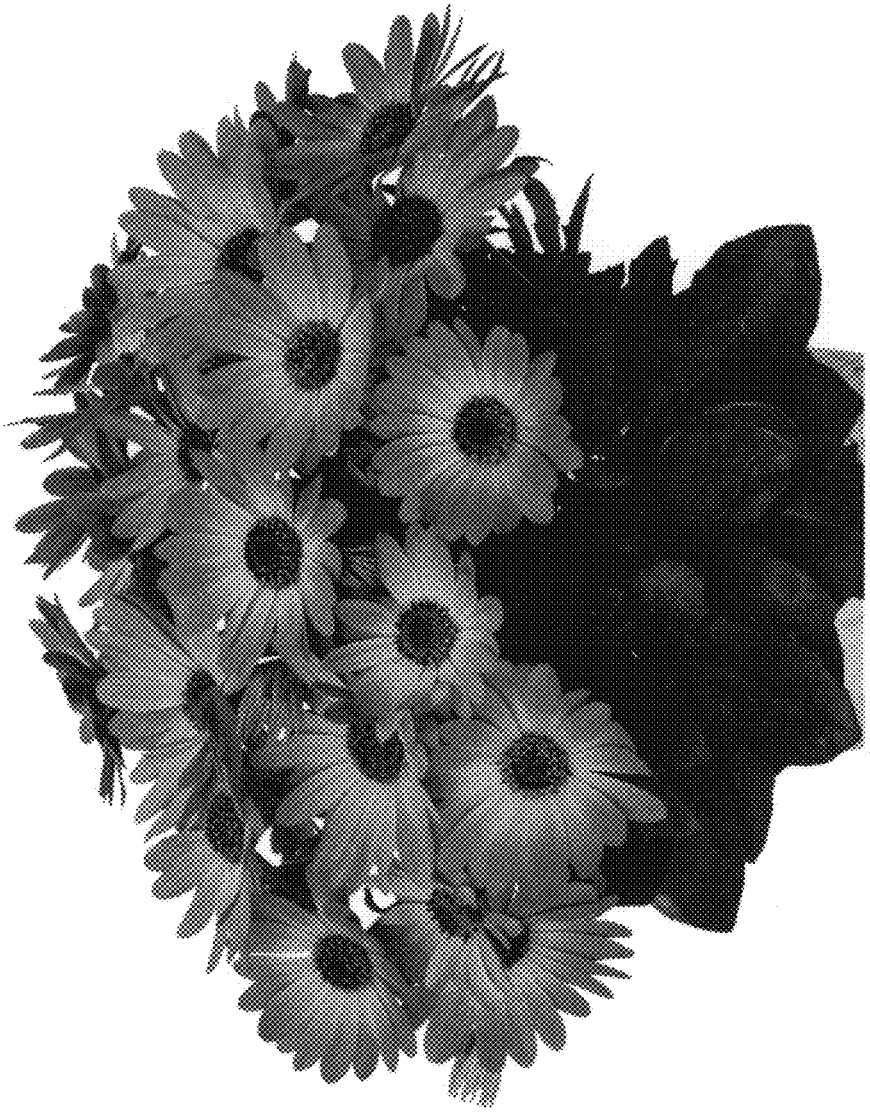

* * * * *